US009439747B2

(12) United States Patent
Danna et al.

(10) Patent No.: US 9,439,747 B2
(45) Date of Patent: Sep. 13, 2016

(54) ADJUSTABLE MEDICAL ASSEMBLY FOR IMPLANT TENSION ADJUSTMENT

(71) Applicant: Boston Scientific Scimed, Inc., Maple Grove, MN (US)

(72) Inventors: Mark Danna, Charlton, MA (US); Kristina Yim Jenkins, Hudson, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 600 days.

(21) Appl. No.: 13/770,561

(22) Filed: Feb. 19, 2013

(65) Prior Publication Data

US 2013/0217954 A1    Aug. 22, 2013

Related U.S. Application Data

(60) Provisional application No. 61/601,816, filed on Feb. 22, 2012.

(51) Int. Cl.
| A61F 2/00 | (2006.01) |
| A61B 17/04 | (2006.01) |
| A61B 17/06 | (2006.01) |
| A61B 17/00 | (2006.01) |
| A61B 17/122 | (2006.01) |

(52) U.S. Cl.
CPC ......... *A61F 2/0045* (2013.01); *A61B 17/0401* (2013.01); *A61B 17/06109* (2013.01); *A61B 17/122* (2013.01); *A61B 2017/00367* (2013.01); *A61B 2017/00805* (2013.01); *A61B 2017/0403* (2013.01); *A61B 2017/0409* (2013.01); *A61B 2017/0456* (2013.01); *A61B 2017/0461* (2013.01); *A61B 2017/0464* (2013.01); *A61F 2002/0072* (2013.01); *A61F 2250/0007* (2013.01)

(58) Field of Classification Search
CPC .............................................. A61B 2017/0479
See application file for complete search history.

(56) References Cited

U.S. PATENT DOCUMENTS 4,938,760 A *  7/1990  Burton et al. ................ 600/29
8,944,990 B2 *  2/2015  Hamel et al. ................ 600/37

(Continued)

FOREIGN PATENT DOCUMENTS

| WO | 2007059199 A2 | 5/2007 |
| WO | 2010065274 A1 | 6/2010 |
| WO | 2010088917 A1 | 8/2010 |

OTHER PUBLICATIONS

Search Report and Written Opinion for International Application Serial No. PCT/US13/27141, mailed Jul. 30, 2013, 13 pages.

*Primary Examiner* — Catherine B Kuhlman
*Assistant Examiner* — Shannon McBride
(74) *Attorney, Agent, or Firm* — Brake Hughes Bellermann LLP

(57) ABSTRACT

The present invention discloses a medical assembly and method to deliver and place a bodily implant inside a patient's body. The medical assembly includes an insertion tool such that a portion of the insertion tool defines a lumen. The medical assembly further includes a carrier configured to be coupled to the insertion tool and including a passageway. The medical assembly also includes a flexible elongate member configured to pass through the passageway of the carrier and the lumen. The elongate member is also configured to be coupled to the bodily implant such that a portion of the elongate member between the bodily implant and the carrier defines a length.

19 Claims, 14 Drawing Sheets

(56) References Cited

U.S. PATENT DOCUMENTS

2010/0324357 A1* 12/2010 Chu ............................ 600/37
2011/0071549 A1* 3/2011 Caborn et al. ............. 606/144
2011/0112357 A1* 5/2011 Chapman et al. ............ 600/37
2012/0316386 A1* 12/2012 Wirbisky ........... A61B 17/0401
600/30

* cited by examiner

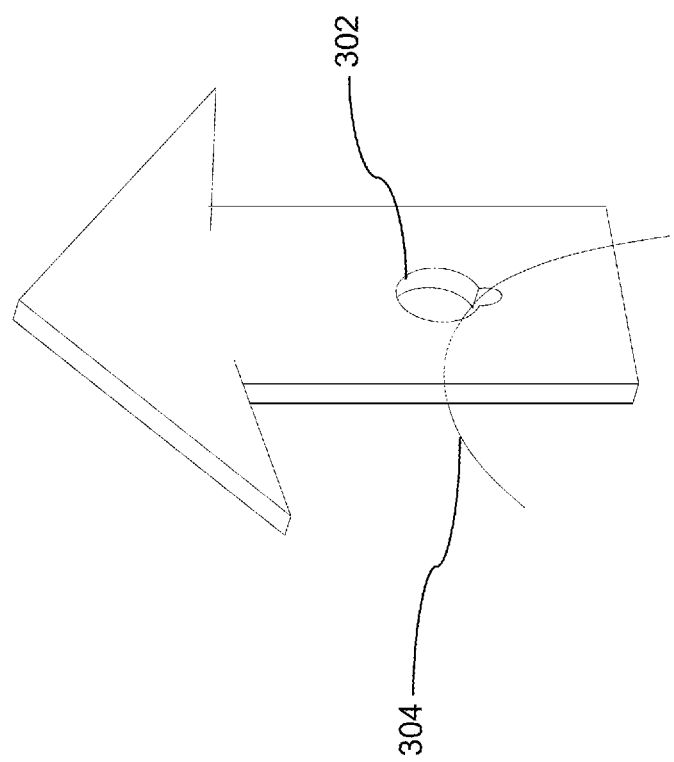

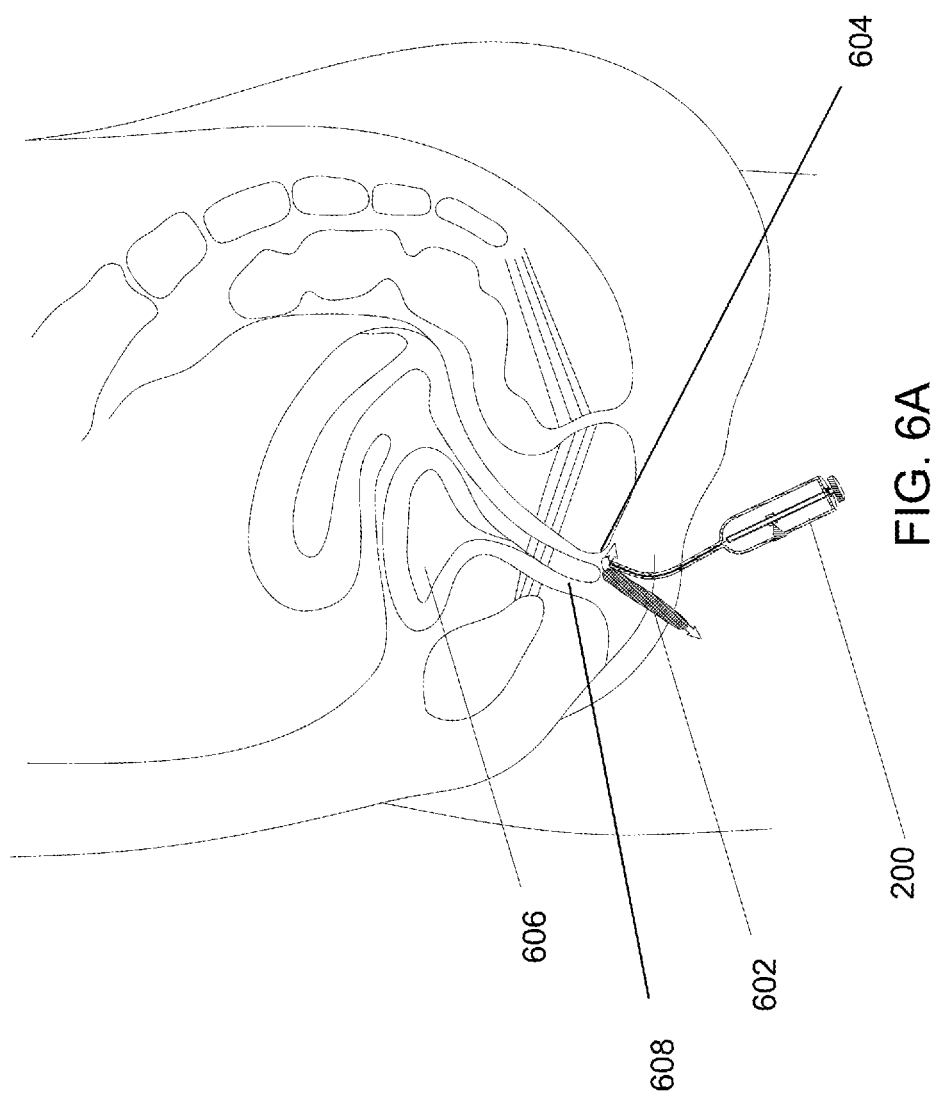

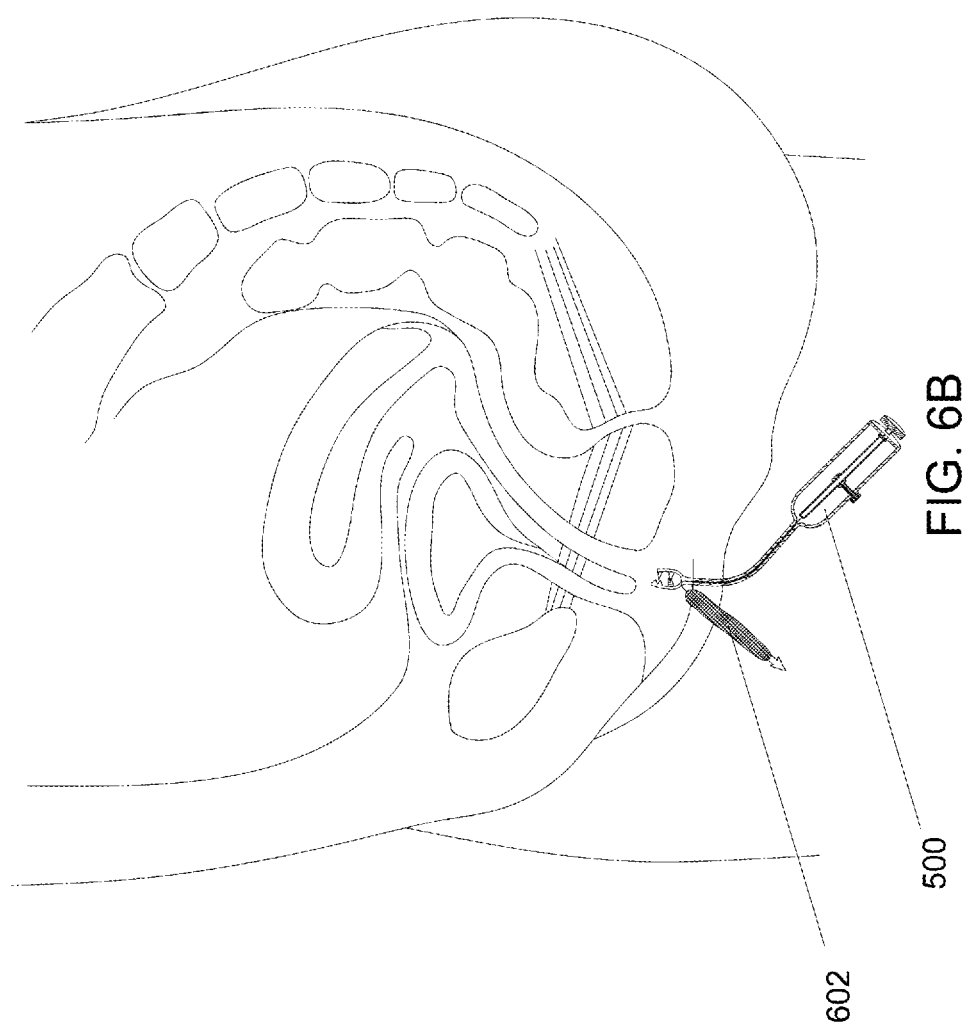

ADJUSTABLE MEDICAL ASSEMBLY FOR IMPLANT TENSION ADJUSTMENT

CROSS-REFERENCE TO RELATED APPLICATION

This application is a Nonprovisional of, and claims priority to, U.S. patent application Ser. No. 61/601,816, filed Feb. 22, 2012, entitled "ADJUSTABLE MEDICAL ASSEMBLY FOR IMPLANT TENSION ADJUSTMENT", which is incorporated by reference herein in its entirety.

BACKGROUND

1. Field

The present invention generally relates to surgical devices and procedures, particularly devices and methods for the delivery, placement and tension adjustment of implants within a patient's body.

2. Description of the Related Art

Anatomical tissues such as pelvic tissues may be weakened or damaged with age, injury, or disease. This decrease in structural integrity of anatomical tissues may have significant medical consequences, which in turn might influence biological functions of the tissues. There are various surgical procedures for treating such dysfunction of the tissues. Implants can be placed into a patient to provide support for the weakened or damaged tissue. The support provided by the implant can mimic the natural position and structure of the tissue, and thereby help decrease or eliminate impairment of biological functions resulting from tissue weakening or damage.

These surgical procedures or methods may use a delivery device to deliver the implant at the anatomical tissue inside the patient's body. Such delivery devices may assist in the delivery and placement of the implant. The existing surgical procedures and devices do not allow the doctor or the operator to test and adjust the tension directly from the delivery device held in a hand of the operator and from outside the patient's body. In view of the above, there is a need of a delivery device and a surgical procedure that facilitates tension adjustment of the implant directly from the delivery device. Further, there is a need for a device and a method that are configured to test and adjust the implant tension pre-operatively (that is before insertion of the device inside the patient's body) in addition to intra-operatively (that is during surgical process).

SUMMARY

The present invention disclosed a medical assembly and method to deliver and place a bodily implant inside a patient's body. The medical assembly includes an insertion tool configured to be inserted into a patient's body. The insertion tool having a proximal end portion and a distal end portion such that a portion between the distal end portion and the proximal end portion defines a lumen. The medical assembly further includes a carrier configured to be coupled to the distal end portion of the insertion tool and configured to be disposed within a bodily tissue upon placement. The carrier includes a passageway.

The medical assembly also includes a flexible elongate member with a proximal end portion and a distal end portion. The elongate member is configured to be disposed within the lumen of the insertion tool. The elongate member is further configured to pass through the passageway of the carrier. The elongate member is also configured to be coupled to the bodily implant such that a portion of the elongate member between the bodily implant and the carrier defines a length of the elongate member.

The insertion tool also includes an adjustment mechanism that is configured to adjust the length of the elongate member between the implant and the carrier and a locking mechanism configured to lock the elongate member within the insertion tool. The length of the elongate member between the carrier and the bodily implant is configured to be fixed by securing the elongate member to the carrier passageway.

BRIEF DESCRIPTION OF THE FIGURES

The invention and the following detailed description of certain embodiments thereof may be understood with reference to the following figures:

FIG. 3A-3D illustrate exemplary ways of securing a portion of an elongate member to a carrier, in accordance with some embodiments of the present invention.

FIG. 6A-6E illustrate delivery of a bodily implant in a patient's body, in accordance with an embodiment of the present invention.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

The terms proximal and distal described in relation to various medical devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like, who may perform the procedure of surgery through the patient's body orifice as described in the present invention. The term proximal refers to an area that is closest to the operator. The term distal refers to an area that is farthest from the operator. The patient referred here can be a human female, male or any other mammal.

Figure 1:
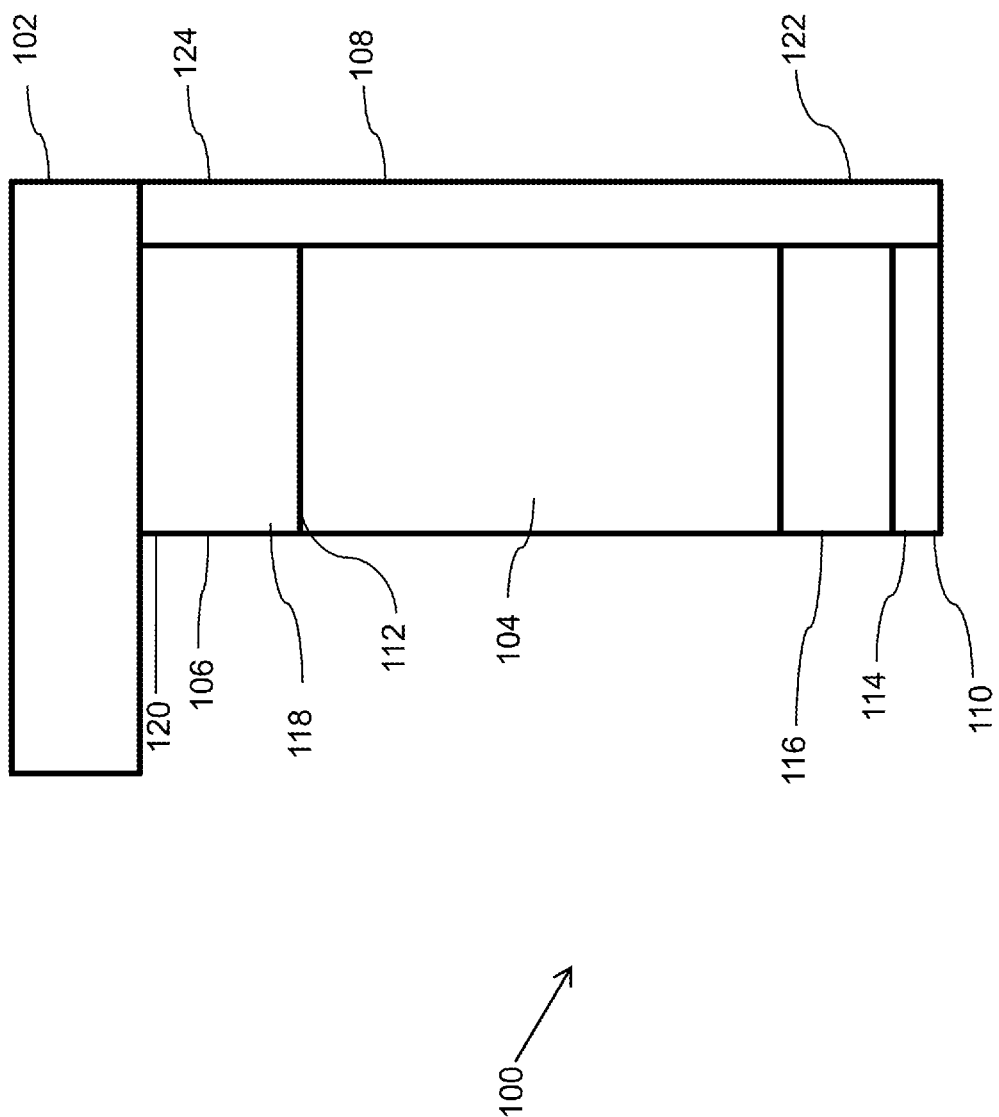
FIG. 1 is a schematic diagram of a medical assembly coupled to a bodily implant, in accordance with an embodiment of the present invention.

FIG. 1 is a schematic diagram of a medical assembly 100 coupled to a bodily implant 102, in accordance with an embodiment of the present invention. The medical assembly 100 is configured to deliver and place the bodily implant 102 inside a patient's body. In some embodiments, the bodily implant 102 is a mesh-based device used to treat patients suffering from pelvic floor disorders such as urinary incontinence.

The medical assembly 100 includes an insertion tool 104, a carrier 106, and a flexible elongate member 108.

The insertion tool 104 is configured to be inserted into a patient's body. The insertion tool 104 has a proximal end portion 110 and a distal end portion 112 such that a portion between the distal end portion 112 and the proximal end portion 110 defines a lumen. In some embodiments, the lumen extends through some portion of the insertion tool 104. In other embodiments, the lumen extends along the complete length of the insertion tool 104.

The insertion tool 104 includes a handle and a needle. The needle is coupled to the handle of the insertion tool 104. In some embodiments, the needle is removably coupled to the handle. In other embodiments, the needle is fixedly coupled to the handle such that the needle and the handle form integral parts of the medical assembly 100. In some embodiments, the needle can be a hypotube. As described above, the lumen may extend through a portion of the needle and the handle in some embodiments. In other embodiments, the lumen may extend through the complete length of the needle and the handle of the insertion tool 104.

In some embodiments, the needle can be made of stainless steel or other medical grade metal. In some embodiments, the handle is made up of a plastic material. Exemplary plastic materials include polycarbonate, lexan, Acrylonitrile butadiene styrene (ABS), and the like without limitations.

The insertion tool 104 further includes an adjustment mechanism 114 and a locking mechanism 116. The adjustment mechanism 114 includes a knob. In some embodiments, the knob is configured to be rotated clockwise and anticlockwise. In other embodiments, the knob is configured to be pushed and pulled inside and outside with respect to the proximal end portion 110 of the insertion tool 104. In still various other embodiments, several other types of mechanisms can be possible within the knob to regulate its movement. The adjustment mechanism 114 including the knob can be located at the proximal end portion 110 of the insertion tool 104. In some embodiments, it can be disposed at medial or any other location.

In some embodiments, the locking mechanism 116 includes a gear and a push button. The push button is configured to engage gear teeth when pushed from a location external to the lumen of the insertion tool. In this manner, the push button or a separate shaft connected to the push button may get engaged with the gear teeth to fix the location of the push button and lock the mechanism. In some embodiments, the locking mechanism 116 may include only one gear. In other embodiments, multiple gears to provide multiple locking facilities from the same locking mechanism can be possible. In various embodiments, the gear may a spur type, a helical type, a worm type, and the like. The locking mechanism may further include locks that are configured to retain the gear in place within the lumen such that the push button or the separate shaft connected to the push button does not get disengaged from the gear.

The medical assembly 100 further includes a carrier 106 having a proximal end portion 118 and a distal end portion 120. The proximal end portion 118 of the carrier 106 is coupled to the distal end portion 112 of the insertion tool 104. The carrier 106 is configured to carry the implant 102 and configured to be disposed within a bodily tissue upon placement. In some embodiments, the carrier 106 is attached to the bodily implant 102 by a heat staking ultra sonic weld or any other type of weld or through a suture loop. For example, a suture with a loop like structure at its end can be used to tie the implant with the carrier 106. In some embodiments, the suture loop or the weld can be configured to provide tensioning adjustments to the implant 102 in the body of the patient. The carrier 106 includes a passageway. The passageway can extend from one edge or surface of the carrier 106 to the other edge or surface of the carrier 106 in various embodiments. For example, in an embodiment, the passageway extends from the proximal end portion 118 of the carrier 106 to a medial location on the carrier 106 such that a lumen or a through channel is defined within the passageway from its proximal end portion 118 to a medial location. In some other embodiments, the passageway can be formed from the proximal end portion 118 to the distal end portion 120 of the carrier 106. Similarly, the passageway can extend to and from any other location on the carrier 106. The passageway can be defined in the form of a slot having different cross sections at different sections. For example, in an embodiment, the slot can have a circular cross section over a portion and a rectilinear cross (that is narrower than the circular cross section) over the remaining portion. Similarly, various other types of slots can be provided.

In some embodiments, the carrier 106 is a dart having a tip portion configured to be fixed to the bodily tissue and configured to anchor the bodily implant 102 with the bodily tissue upon placement. The dart is configured to be coupled to the bodily implant 102 and the insertion tool 104. In some embodiments, the dart can be tubular in shape. In some other embodiments, the dart can have a flat surface.

In other embodiments, the carrier 106 is a clamp configured to be fixed with the bodily tissue such as obtruator muscle. The clamp is configured to be coupled to the distal end portion 112 of the insertion tool 104 at its proximal end. The clamp can include a jaw having flaps configured to come in contact with one another, thereby clamping to the bodily tissue. The clamp can further include a locking member configured to lock the flaps of the jaw into the bodily tissue. In some embodiments, the actuation of the clamp can be controlled with the use of the adjustment member 114. In some embodiments, the clamp can be removably coupled to the insertion tool 104 at the distal end portion 112 of the insertion tool 104.

In some embodiments, the carrier 106, as discussed above, is a first carrier that is configured to be attached to a first bodily tissue. The medical assembly 100 may further include a second carrier that is configured to be attached to a second bodily tissue. In some embodiments, the first carrier is configured to be coupled to a first end portion of the bodily implant 102. And the second carrier is configured to be coupled to a second end portion of the bodily implant 102. The first and second carriers can be similar or different. In some embodiments, the first carrier is a dart and the second carrier is also a dart similar to the first carrier. In some other embodiments, the first carrier is a dart and the second carrier is a clamp similar to the clamp discussed above. In still other embodiments, the first carrier can be adjustable while the second carrier is fixed and just configured to be fixed to the bodily tissue, but not configured to make any tension adjustments. In still other embodiments, both the first and second carriers can be adjustable.

In some embodiments, the carrier 106 is made of a polypropylene material. In some embodiments, the carrier 106 can be made of a material selected at least from the group consisting of a plastic, a bio absorbable, a radiopaque, a medical grade stainless steel, an Acrylonitrile butadiene styrene, and a polycarbonate.

As discussed above, the medical assembly 100 further includes the elongate member 108. The elongate member 108 can be one of a thread, suture, fiber, or any other flexible member. The elongate member 108 is configured to pass across lumens, slots, and passageways and to flexibly tie and couple different members or elements or devices.

The elongate member 108 includes a proximal end portion 122 and a distal end portion 124. The distal end portion 124 of the elongate member 108 is configured to be disposed within the lumen of the insertion tool 104 and extend through the passageway formed into the carrier 106. Further, the distal end portion 124 of the elongate member 108 is configured to be coupled to the bodily implant 102 such that a portion of the elongate member 108 between the bodily implant 102 and the carrier 106 defines a length of the elongate member 108. This defined length can be termed as a tensioning length merely for the purpose of description of the invention since it is configured to adjust tension in the bodily implant 102 once the bodily implant 102 is placed inside the body. In some embodiments, the elongate member 108 is monofilament. In other embodiments, the elongate member 108 includes knots at discrete locations over a portion of the elongate member 108.

In some embodiments, the bodily implant 102, as described above, is formed of a material that allows tissue in-growth after implantation. Various types of woven tapes, fabrics, or meshes may be utilized in fabricating and manufacturing the bodily implant 102, in accordance with various embodiments of the present invention. In some embodiments, the bodily implant 102 can be a mesh-based device. The mesh-based device may utilize a variety of mesh materials and may be designed in a variety of forms. An example of a mesh utilized in the mesh-based device is Polyform® Synthetic Mesh developed by the Boston Scientific Corporation. The Polyform® Synthetic Mesh is made from uncoated monofilament macro-porous polypropylene.

The implant 102 can be made of a material at least one selected from a group consisting of a polypropylene, other plastic material, biologic of bovine dermis, porcine dermis, cellulose based product, allograft, and its equivalent. The mesh may also be made from other biological materials or cadaveric tissues. Typically, the mesh-based device has a smooth surface to avoid/reduce irritation on adjacent body tissues during mesh-tissue interactions. Additionally, the mesh-based device is stretchable and flexible to adapt movements along the anatomy of the human body and reduce suture pullout. In an embodiment, the bodily implant 102 can have a coating. For example, the implant 102 can be coated with an antimicrobial agent and/or an antifungal agent. In accordance with various other embodiments, several other kinds of implants can be employed within the medical assembly 100 of the present invention for the treatment of several kinds of pelvic floor disorders.

The tension of the implant 102 is adjusted through the adjustment mechanism 114 of the insertion tool 104 by changing the length of the elongate member 108 between the carrier 106 and the bodily implant 102. Once the desired length of the elongate member 108 between the carrier 106 and the bodily implant 102 is achieved, the locking mechanism 116 locks the elongate member 108 within the insertion tool 104. In an embodiment, the adjusting and locking of the length between the carrier 106 and the bodily implant 102 can be done before the placement of the bodily implant 102 inside the patient's body. In another embodiment, the adjusting and locking of the length between the carrier 106 and the bodily implant 102 can be done intra-operatively (that is during surgery) after the implant 102 has been placed inside the patient's body or during its placement. Furthermore, the elongate member 108 between the carrier 106 and the bodily implant 102 is configured to be secured within the passageway of the carrier 106. Various methods of securing the length between the carrier 106 and the bodily implant 102 at the passageway are described in conjunction with FIGS. 3A-3C and 7 later.

Figure 2:
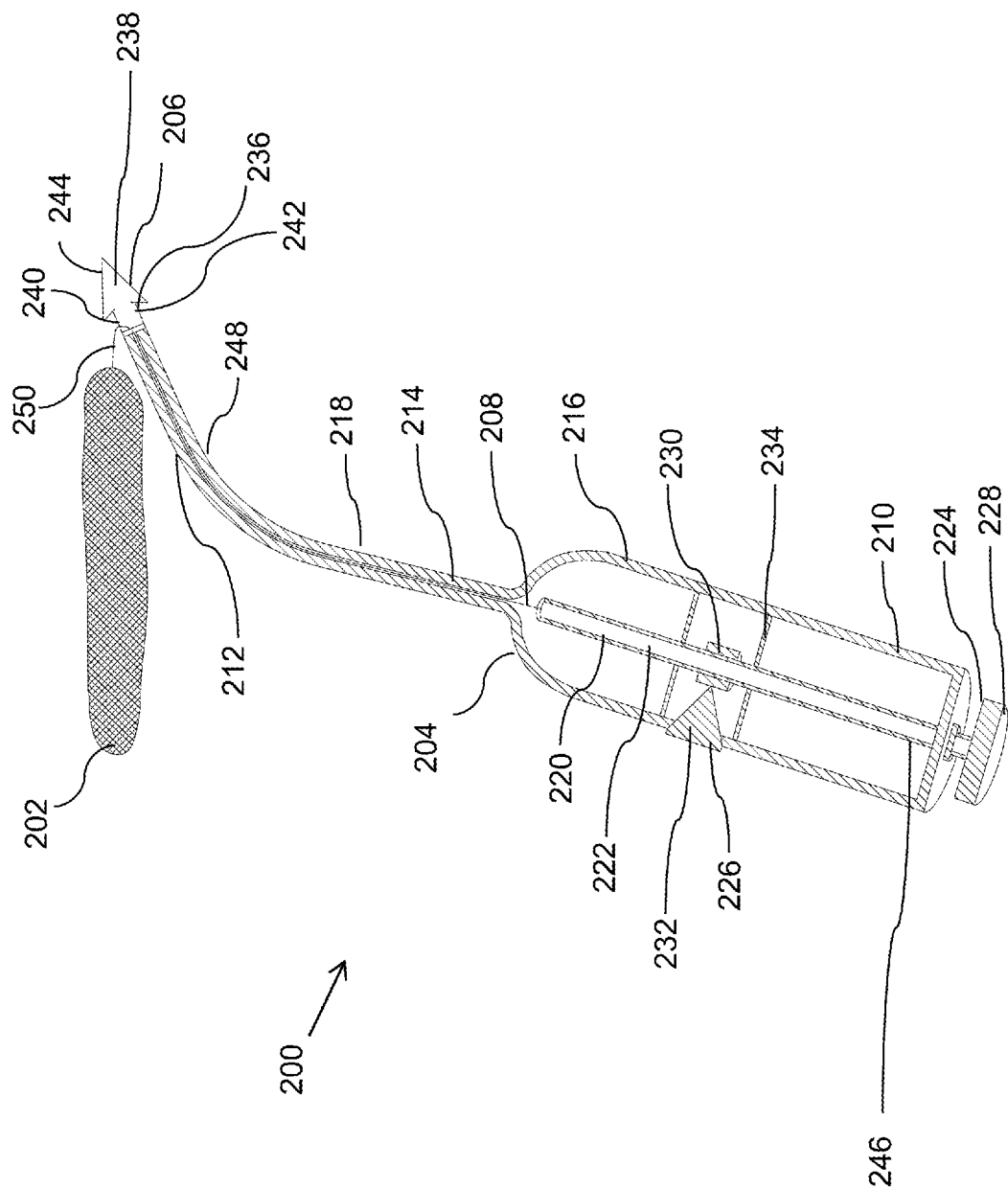
FIG. 2 is a perspective view of a medical assembly coupled to a bodily implant, in accordance with an embodiment of the present invention.

The length of the elongate member 108 between the carrier 106 and the bodily implant 102 can be adjusted and locked from within the insertion tool 104, in accordance with at least some embodiments of the present invention. Therefore, the operator can adjust this length while inserting the insertion tool 104 inside the patient's body or prior to insertion from the insertion tool 104 itself. Therefore, no external device or arrangement may be required to adjust the length between the carrier 106 and the bodily implant 102 and hence, the tension of the bodily implant 102 within the patient's body can be adjusted from the insertion tool 104 itself FIG. 2 is a perspective view of a medical assembly 200 coupled to a bodily implant 202, in accordance with an embodiment of the present invention. The medical assembly 200 is configured to deliver and place the bodily implant 202 inside a patient's body. In some embodiments, the bodily implant 202 is a mesh-based device used to treat patients suffering from pelvic floor disorders such as urinary incontinence.

The medical 200 includes an insertion tool 204, a carrier 206, and a flexible elongate member 208.

The insertion tool 204 is configured to be inserted into a patient's body. The insertion tool 204 has a proximal end portion 210 and a distal end portion 212 such that a portion between the distal end portion 212 and the proximal end portion 210 defines a lumen 214. In some embodiments, the lumen 214 extends through some portion of the insertion tool 204. In other embodiments, the lumen 214 extends along the complete length of the insertion tool 204.

The insertion 204 includes a handle 216 and a needle 218. The needle 218 is coupled to the handle 216 of the insertion tool 204. In some embodiments, the needle 218 is removably coupled to the handle 216. In other embodiments, the needle 218 is fixedly coupled to the handle 216 such that the needle 218 and the handle 216 form integral parts of the medical assembly 200. As described above, the lumen 214 may extend through a portion of the needle 218 and the handle 216 in some embodiments. In other embodiments, the lumen 214 may extend through the complete length of the needle 218 and the handle 216 of the insertion tool 204. In some embodiments, the handle 216 is made up of a plastic material. Exemplary plastic materials include polycarbonate, lexan, Acrylonitrile butadiene styrene (ABS), and the like without limitations.

The needle 218 can be made of stainless steel or other medical grade metal. In some embodiments, the needle 218 is bent or curved to at least some portion as illustrated in FIG. 2. In some embodiments, the distal end of the needle 218 is configured to be coupled to the carrier 206. For example, a portion of the carrier 206 may be configured to be disposed into the lumen of the needle 218 to couple it with the needle 218. The portion of the carrier 206 that is configured to be disposed inside the lumen may have a slightly lesser diameter or width as compared to rest of the carrier portion. This may allow a friction fitting of the carrier 206 within the lumen. In accordance with various embodiments, various types of release mechanisms that are configured to release the carrier 206 from the lumen of the needle 218 can be provided. For example, in an embodiment, the carrier may include a projection and an inner surface of the needle lumen may include a recess to conform to the shape of the projection and configured to receive the projection therein. When the carrier 206 is inserted within the lumen, the projection may get fitted into the recess and thus couple the carrier 206 to the needle 218. Also, after the implant has been placed inside the body, the projection can be released from the recess for example by pulling the carrier 206 against the tissue. A force exerted on the carrier 206 in a specific direction may release the projection thus releasing the carrier 206 from the needle 218. It must be appreciated that pulling the carrier 206 in one direction with respect to the distal end portion of the needle 218 may cause releasing of the projection while pushing the carrier 206 in the lumen in another direction (substantially opposite the first direction) with respect to the distal end portion of the needle 218 may cause fitting of the projection within the recess.

In some other embodiments, a mere push or pull on the carrier 206 may be responsible for fitting the carrier 206 into the lumen or releasing the carrier 206 from the lumen. In such cases, a surgeon may for example insert the carrier 206 in the lumen in a manner as described above. And, releasing of the carrier 206 can be done by pulling the carrier 206 against the tissue. In such embodiments, the coupling of the carrier 206 within the lumen may not be tight fit. There can be provided a sufficient buffer in the coupling so that the carrier 206 could be released when an adequate force that can be easily generated by pulling it against the tissue is applied.

The insertion tool 204 further includes a shaft 220. The shaft is disposed within the handle 216. The shaft 220 further includes a lumen 222 such that a flexible member such as a suture or a thread and the like can be passed through the lumen 222 of the shaft 220. The shaft lumen 222 can extend through at least some portion of the shaft 220 longitudinally. In some embodiments, the shaft 220 can be coupled to the handle 216 fixedly. In other embodiments, the shaft 220 can be removably disposed within the handle 216.

The insertion tool 204 further includes an adjustment mechanism 224 and a locking mechanism 226. The adjustment mechanism 224 includes a knob 228. In some embodiments, the knob 228 is configured to be rotated clockwise and anticlockwise. In other embodiments, the knob 228 is configured to be pushed and pulled inside and outside with respect to the proximal end portion 210 of the insertion tool 204. In still various other embodiments, several other types of mechanisms can be possible within the knob 228 to regulate its movement. The adjustment mechanism 224, including the knob 228 can be located at the proximal end portion 210 of the insertion tool 204. In some embodiments, it can be disposed at medial or any other location.

As illustrated in FIG. 2, the adjustment mechanism 224 is coupled to the shaft 220 that is disposed within the handle 216. In accordance with some embodiments, the shaft 220 can be an integral part of the adjustment mechanism 224 such that the shaft 220 extends directly and integrally from the knob 228 of the adjustment mechanism 224. However, in some other embodiments, the shaft 220 may be a separate member and configured to be removably attached to the handle 216 or the knob 228 of the adjustment mechanism 224. The adjustment mechanism may further include a lock. The lock is configured to lock the adjustment mechanism 224 in place. For example, in some embodiments, the lock can be a friction lock that is configured to lock the adjustment mechanism 224 upon a push or a pull. In other embodiments, the lock can be a thread lock having a set of male threads that are configured to engage female threads provided on the shaft 220 and lock the adjustment mechanism 224 in place upon rotation.

As Illustrated in FIG. 2, the locking mechanism 226 includes a gear 230 and a push button 232. The push button 232 is configured to engage gear teeth when pushed from a location external to the lumen of the insertion tool 204. In this manner, the push button 232 or a separate shaft connected to the push button 232 may get engaged with the gear teeth to fix the location of the push button 232 and lock the mechanism. In some embodiments, the locking mechanism 226 may include only one gear. In other embodiments, multiple gears to provide multiple locking facilities from the same locking mechanism can be possible. In various embodiments, the gear 230 may a spur type, a helical type, a worm type, and the like. A lock or multiple locks 234 can be provided in the locking mechanism 226 that get(s) locked upon gear 230 engagement. The locks are configured to retain the gear in place within the lumen 214 such that the push button 232 or a separate shaft connected to the push button 232 does not get disengaged from the gear 230.

Figure 3A:
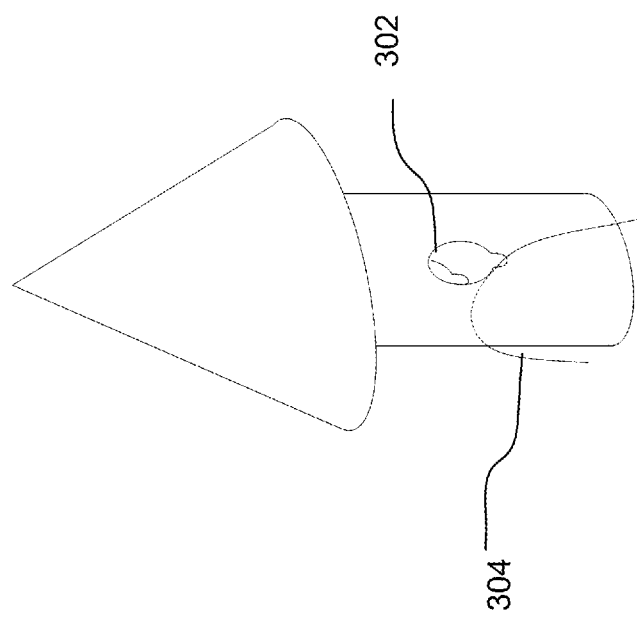
Figure 3B:
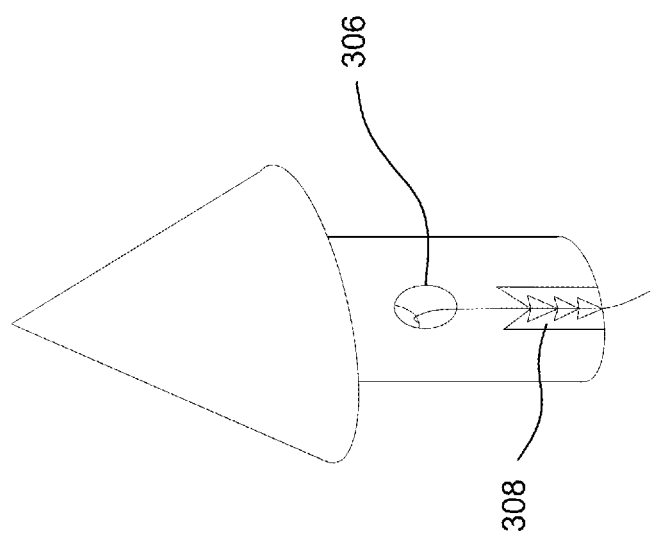
Figure 3C:
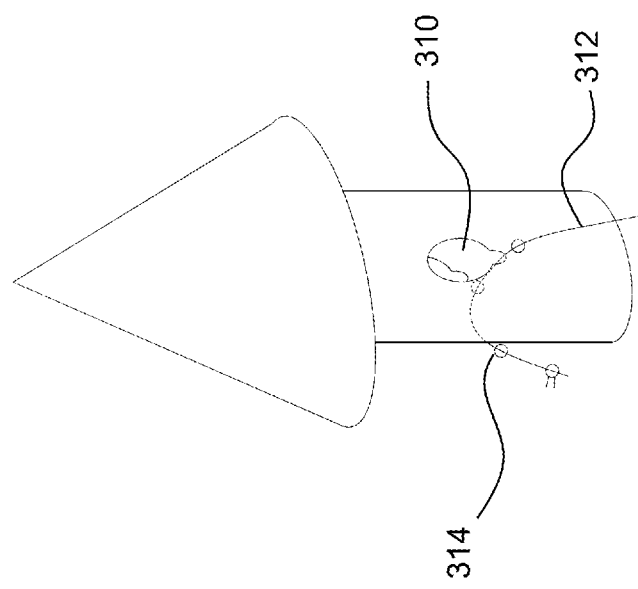

The medical assembly 200 further includes a carrier 206 having a proximal end portion 236 and a distal end portion 238. The proximal end portion 236 of the carrier 206 is coupled to the distal end portion 212 of the insertion tool 204. The carrier 206 is configured to carry the implant 202 and is configured to be disposed within a bodily tissue upon placement. In some embodiments, the carrier 206 is a dart having a tip portion configured to be fixed to the bodily tissue and configured to anchor the bodily implant 202 with the bodily tissue upon placement. In some embodiments, the dart can be tubular in shape as shown in FIGS. 3A-3C. In some other embodiments, the dart can have a flat surface as shown in FIG. 3D.

In some embodiments, the carrier 206 includes a passageway 240. The passageway 240 can extend from one edge or surface of the carrier 206 to the other edge and surface of the carrier 206 in various embodiments. For example, in an embodiment, the passageway 240 extends from the proximal end portion 236 of the carrier 206 to a medial location on the carrier 206 such that a lumen or a through channel is defined within the passageway 240 from its proximal end portion 236 to a medial location on its lateral surface. In some other embodiments, the passageway 240 can be formed from the proximal end portion 236 to the distal end portion 238 of the carrier 206. Similarly, the passageway 240 can extend to and from any other location on the carrier 206.

The passageway 240 can be defined in the form of a slot having different cross sections at different sections. In an embodiment, the slot can have a substantially circular cross section 302 at one end and a rectilinear cross section 304 at the other end such that the rectilinear cross section 304 is narrower than the circular cross section 302 as shown in FIG. 3A. In another embodiment, the passageway 240 of the carrier 206 includes a slot with a circular cross section 306 and a teethed section 308 having teeth configured to engage the elongate member 208 that passes through the circular section 306 and the teethed section 308 as shown in FIG. 3B. In still another embodiment, as shown in FIG. 3C, the passageway 240 of the carrier 206 is defined by a slot with a substantially circular cross section 310 at one end and a rectilinear cross section 312 at the other end such that the rectilinear cross section is narrower than the circular cross section. In this case, the elongate member 208 is further configured to pass the slot and includes at least one knot 314 present at discrete locations on a portion of the elongate member 208. FIGS. 3A-3C show the carrier 206 with a tubular cross-section and FIG. 3D show the carrier 206 with a rectangular cross-section. It must be appreciated that the carrier 206 may have or any other type of cross-section in several other embodiments.

Referring again to FIG. 2, in accordance with the illustrated embodiments, the carrier 206 is a dart having a tip portion configured to be fixed to the bodily tissue and configured to anchor the bodily implant 202 with the bodily tissue upon placement.

The dart 206 has a proximal end portion 242 and a distal end portion 244. The distal end portion 244 is configured to be coupled to the bodily implant 202 via the elongate member 208. For example, the elongate member 208 may pass through the passageway 240 of the dart 206 and then coupled to the implant 202, and thus hold the dart 206 and the implant 206 together. In some embodiments, the dart 206 may include a portion that is configured to be disposed within the lumen 214 of the insertion member 204.

In some embodiments, the carrier 206 as discussed above is a first carrier that is configured to be attached to a first bodily tissue. The medical assembly 200 may further include a second carrier that is configured to be attached to a second bodily tissue. In some embodiments, the first carrier 206 is configured to be coupled to a first end portion of the bodily implant 202. And, the second carrier is configured to be coupled to a second end portion of the bodily implant 202. The first and second carriers can be similar or different. In some embodiments, the first carrier is a dart and the second carrier is also a dart similar to the first carrier. In some other embodiments, the first carrier is a dart and the second carrier is a clamp similar to the clamp discussed above in conjunction with FIG. 1. In still other embodiments, the first carrier can be adjustable while the second carrier is fixed and configured to be fixed to the bodily tissue, but not configured to make any tension adjustments. In still other embodiments, both of the first and second carriers can be adjustable.

In some embodiments, the carrier 206 is made of a polypropylene material. In some embodiments, the carrier 206 can be made of a material selected at least from the group consisting of a plastic, a bio absorbable, a radiopaque, a medical grade stainless steel, an Acrylonitrile butadiene styrene and a polycarbonate.

As discussed above, the medical device 200 further includes the elongate member 208. The elongate member 208 can be one of a thread, suture, fiber, or any other flexible member. The elongate member 208 is configured to pass across lumens, slots, and passageways and to flexibly tie and couple different members or elements or devices. The elongate member 208 includes a proximal end portion 246 and a distal end portion 248. The distal end portion 248 of the elongate member 208 is configured to be disposed within the lumen 214 of the insertion tool 204 and extend through the passageway 240 formed into the carrier 206. Further, the distal end portion 248 of the elongate member 208 is configured to be coupled to the bodily implant 202 such that a portion of the elongate member 208 (between the bodily implant 202 and the carrier 206) defines a length 250 of the elongate member 208. This length 250 can be termed as a tensioning length merely for the purpose of description of the invention since it is configured to adjust tension in the bodily implant 202 once the bodily implant 202 is placed inside the body. In some embodiments, the elongate member 208 is monofilament. In other embodiments, the elongate member 208 can be a braided suture loop. The braided suture loop includes knots at discrete locations over a portion of the elongate member 208.

Figure 4:
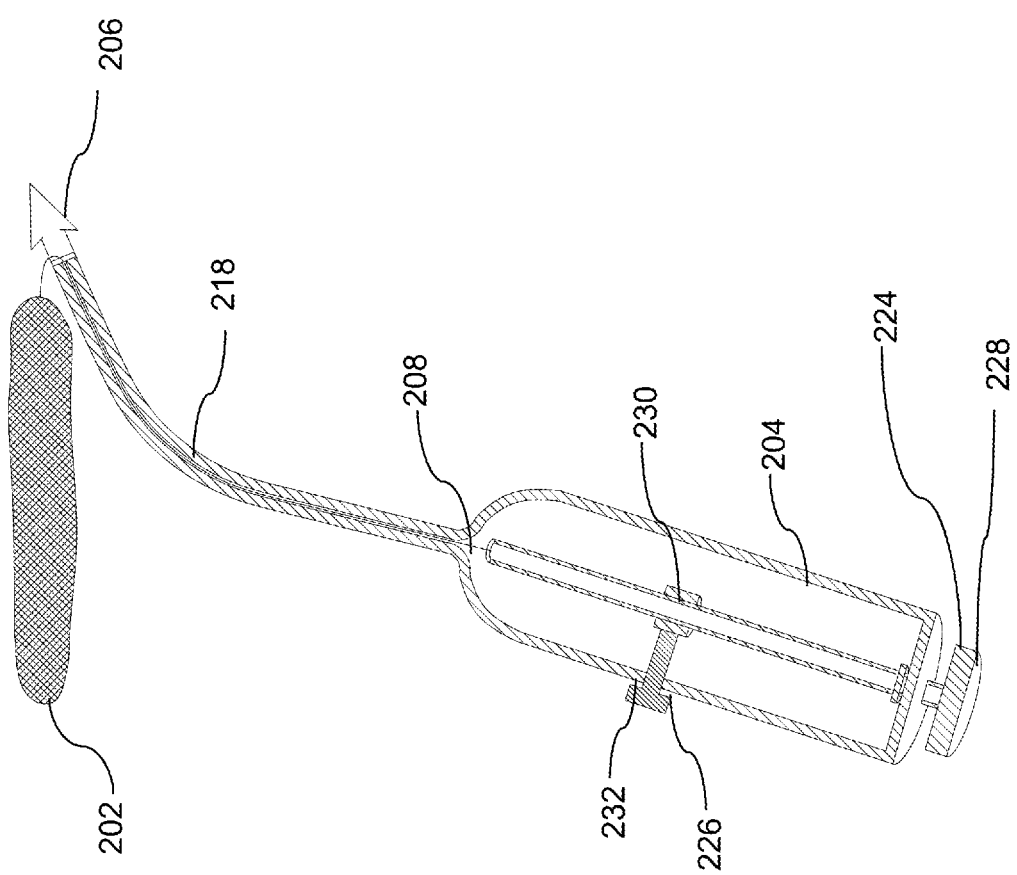
FIG. 4 is a perspective view of a medical assembly coupled to a bodily implant, in accordance with an embodiment of the present invention.

The adjustment mechanism 224 and locking mechanism 226, as described above, in conjunction with FIG. 2 are merely exemplary and several other types of mechanisms (that are configured to adjust the length 250 of the elongate member 208 between the bodily implant 202 and the carrier 206) can be employed in the insertion tool 204. For example, another type of adjustment and locking mechanism with another shape of the push button that can be employed in the medical assembly 200 has been illustrated in FIG. 4. Similarly, various other shapes of the push button 232, the adjustment mechanism 224, and the locking mechanism 226 can also be possible in accordance with various embodiments.

Figure 5:
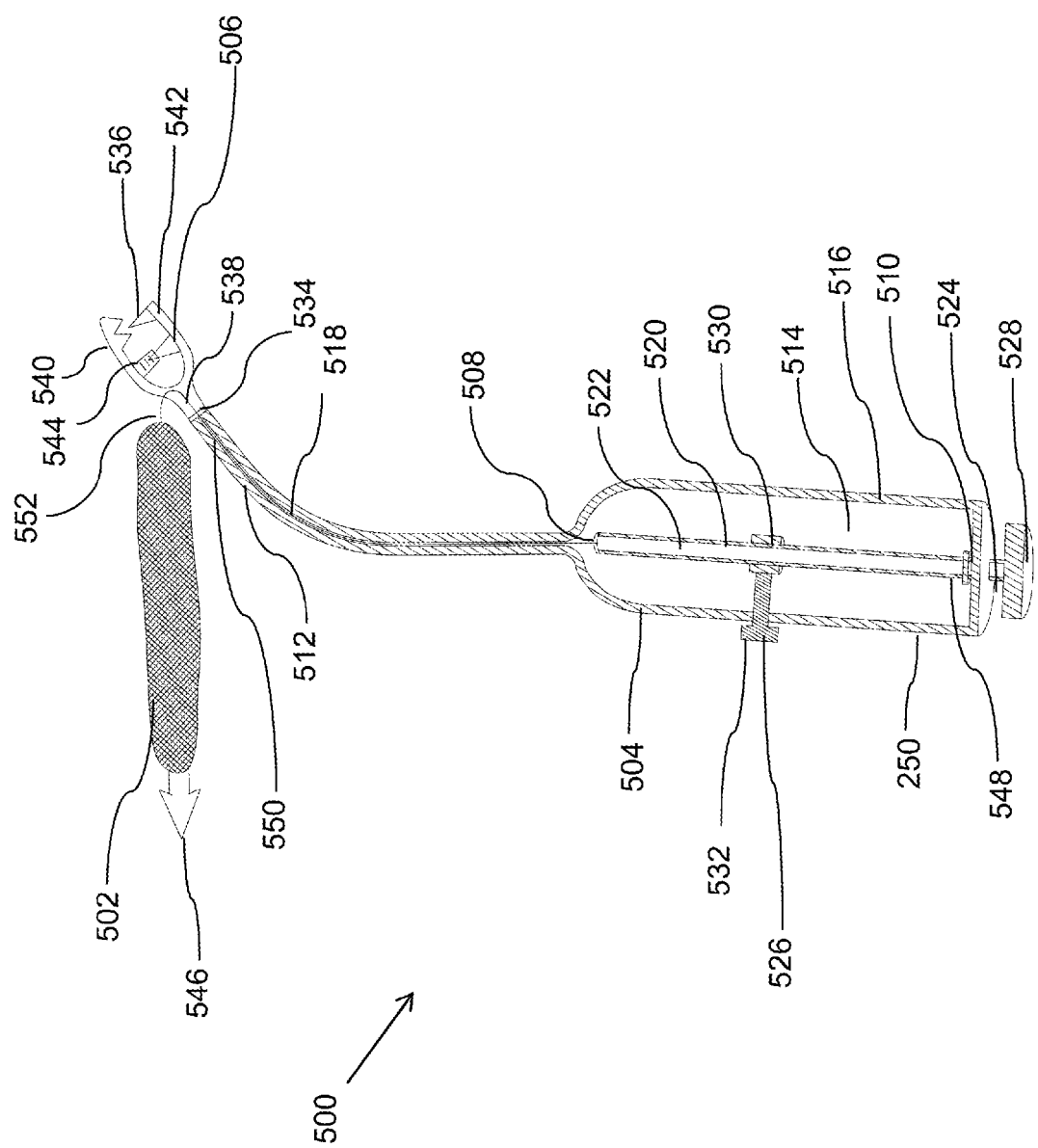
FIG. 5 is a perspective view of a medical assembly coupled to a bodily implant, in accordance with an embodiment of the present invention.

FIG. 5 is a perspective view of a medical assembly 500 coupled to a bodily implant 502, in accordance with an embodiment of the present invention. The medical assembly 500 includes an insertion tool 504, a carrier 506, and a flexible elongate member 508.

The insertion tool 504 is configured to be inserted into a patient's body. The insertion tool 504 has a proximal end portion 510 and a distal end portion 512 such that a portion between the distal end portion 512 and the proximal end portion 510 defines a lumen 514. In some embodiments, the lumen 514 extends through some portion of the insertion tool 504. In other embodiments, the lumen 514 extends along the complete length of the insertion tool 504.

The insertion tool includes a handle 516 and a needle 518. The needle 518 is coupled to the handle 516 of the insertion tool 504. In some embodiments, the needle 518 is removably coupled to the handle 516. In other embodiments, the needle 518 is fixedly coupled to the handle 516 such that the needle 518 and the handle 516 form integral parts of the medical assembly 500. In some embodiments, the needle 518 can be made of stainless steel or other medical grade metal. In some embodiments, the needle 518 is bent or curved to at least some portion as illustrated in FIG. 5. As described above, the lumen 514 may extend through a portion of the needle 518 and the handle 516 in some embodiments. In other embodiments, the lumen 514 may extend through the complete length of the needle 518 and the handle 516 of the insertion tool 504. In some embodiments, the handle 516 is made up of a plastic material. Exemplary plastic materials include polycarbonate, lexan, Acrylonitrile butadiene styrene (ABS), and the like without limitations.

The insertion tool 504 further includes a shaft 520. The shaft 520 is disposed within the handle 516. The shaft 520 further includes a lumen 522 such that a flexible member such as a suture or a thread and the like can be passed through the lumen 522 of the shaft 520. The shaft lumen 522 can extend through at least some portion of the shaft 520 longitudinally. In some embodiments, the shaft 520 can be coupled to the handle 516 fixedly. In other embodiments, the shaft 520 can be removably disposed within the handle 516.

The insertion tool 504 further includes an adjustment mechanism 524 and a locking mechanism 526. The adjustment mechanism 524 includes a knob 528. In some embodiments, the knob 528 is configured to be rotated clockwise and anticlockwise. In other embodiments, the knob 528 is configured to be pushed and pulled inside and outside with respect to the proximal end portion 510 of the insertion tool 504. In still various other embodiments, several other types of mechanisms can be possible within the knob 528 to regulate its movement. The adjustment mechanism 524 including the knob 528 can be located at the proximal end portion 510 of the insertion tool 504. In some embodiments, it can be disposed at medial or any other location.

As illustrated in FIG. 5, the adjustment mechanism 524 is coupled to the shaft 520 that is disposed within the handle 516. In accordance with some embodiments, the shaft 520 can be an integral part of the adjustment mechanism 524 such that the shaft 520 extends directly and integrally from the knob 528 of the adjustment mechanism 524. However, in some other embodiments, the shaft 520 may be a separate member and configured to be removably attached to the handle 516 or the knob 528 of the adjustment mechanism 524.

As Illustrated in FIG. 5, the locking mechanism 526 includes a gear 530 and a push button 532. The push button 532 is configured to engage gear teeth when pushed from a location external to the lumen of the insertion tool 504. In this manner, the push button 532 or a separate shaft 520 connected to the push button 532 may get engaged with the gear teeth to fix the location of the push button 532 and lock the mechanism. In some embodiments, the locking mechanism 526 may include only one gear 530. In other embodiments, multiple gears 530 to provide multiple locking facilities from the same locking mechanism 526 can be possible. In various embodiments, the gear 530 may a spur type, a helical type, a worm type, and the like.

The medical assembly 500 further includes the carrier 506 having a proximal end portion 534 and a distal end portion 536. The proximal end portion 534 of the carrier 506 is coupled to the distal end portion 512 of the insertion tool 504. The carrier 506 is configured to carry the implant 502 and configured to be disposed within a bodily tissue upon placement.

The carrier 506 includes a passageway 538. The passageway 538 can extend from one edge or surface of the carrier 506 to the other edge or surface of the carrier 506, in various embodiments. For example, in an embodiment, the passageway 538 extends from the proximal end portion 534 of the carrier 506 to a medial location on the carrier 506 such that a lumen or a through channel is defined within the passageway 538 from its proximal end portion 534 to a medial location on its lateral surface. In some other embodiments, the passageway 538 can be formed from the proximal end portion 534 to the distal end portion 536 of the carrier 506. Similarly, the passageway 538 can extend to and from any other location on the carrier 506.

The passageway 538 can be defined in the form of a slot having different cross sections at different sections. The slot can be similar to those illustrated in conjunction with FIGS. 3A, 3B, and 3C.

In accordance with the illustrated embodiment, the carrier 506 is a clamp configured to be fixed with the bodily tissue such as obtruator muscle. The clamp is configured to be coupled to the distal end portion 512 of the insertion tool 506 at its proximal end 534. The clamp includes a jaw 540 having flaps 542 configured to come in contact with one another, thereby clamping to the bodily tissue. The clamp further includes a locking member 544 configured to lock the flaps 542 of the jaw 540 into the bodily tissue. The locking and unlocking of the flaps 542 can be done by such as actuating the clamp. In some embodiments, the actuation of the clamp can be controlled with the use of the adjustment member 524. For example, in some embodiments, the clamp can be actuated by pulling the knob 528 of the adjustment member 524. The clamp can be removably coupled to the insertion tool 504 at the distal end portion of the insertion tool.

In some embodiments, the carrier 506 as discussed above is a first carrier 506 that is configured to be attached to a first bodily tissue. The medical assembly may further include a second carrier 546 that is configured to be attached to a second bodily tissue. In some embodiments, the first carrier 506 is configured to be coupled to a first end portion of the bodily implant 502. Furthermore, the second carrier 546 is configured to be coupled to a second end portion of the bodily implant 502.

The first and second carriers 506 and 546 can be similar or different. In some embodiments, the first carrier 506 is a dart as illustrated in FIG. 2 and the second carrier 546 is also a dart similar to the first carrier 506. In some other embodiments, the first carrier 506 is a dart and the second carrier 546 is a clamp as illustrated in FIG. 5 and discussed above. In still other embodiments, the first carrier 506 can be adjustable, while the second carrier 546 is fixed and configured to be fixed to the bodily tissue but not configured to make any tension adjustments. In still other embodiments, both of the first and second carriers 506 and 546 can be adjustable.

In some embodiments, the carrier 506 is made of a polypropylene material. In some embodiments, the carrier 506 can be made of a material selected at least from the group comprising a plastic, a bio absorbable, a radiopaque, a medical grade stainless steel, an Acrylonitrile butadiene styrene and a polycarbonate material.

As discussed above, the medical assembly 500 further includes the elongate member 508. The elongate member 508 can be one of a thread, suture, fiber, or any other flexible member. The elongate member 508 is configured to pass across lumens, slots, and passageways and to flexibly tie and couple different members or elements or devices.

The elongate member 508 includes a proximal end portion 548 and a distal end portion 550. The distal end portion 550 of the elongate member 508 is configured to be disposed within the lumen 514 of the insertion tool 504 and extend through the passageway 538 formed into the carrier 506. Further, the distal end portion 552 of the elongate member 508 is configured to be coupled to the bodily implant 502 such that a portion of the elongate member 508 between the bodily implant 502 and the carrier 506 defines a length 552 of the elongate member 508. This length 552 can be termed as a tensioning length merely for the purpose of description of the invention since it is configured to adjust tension in the bodily implant 502 once the bodily implant 502 is placed inside the body. In some embodiments, the elongate member 508 is monofilament. In other embodiments, the elongate member 508 can be a braided suture loop. The braided suture loop includes knots at discrete locations over a portion of the elongate member 508.

FIGS. 6A-6E illustrate delivery and placement of a bodily implant 602 inside a patient's body with the use of a medical assembly such as the medical assembly 200, 500, and the like. The body portions of the patient such as a vagina 604, a bladder 606, a urethra 608, obturator muscles 610, and a pubic bone 612 are also illustrated in FIGS. 6A-6E.

FIG. 6A illustrates insertion of the medical assembly 200 within a patient's body, in accordance with an embodiment of the present invention. As shown, the point of insertion of the medical assembly 200 in accordance with the illustrated embodiment is the vagina 604 of a patient. The tip portion of the insertion tool 204 is inserted inside the body through the vaginal opening 604 (vagina). FIG. 6A illustrates insertion of the medical assembly 200; however the medical assembly 500 can also inserted in a similar manner. The insertion of the medical assembly 500 is illustrated in FIG.

6B. In accordance with this embodiment, at least one of the darts is replaced by a clamp that acts as the carrier 506. FIG. 6B illustrates the clamp coupled at one end portion of the bodily implant 602 while the second end portion has a dart. However, in several other embodiments, the second end portion can also include a clamp instead of the dart.

Figure 6C:
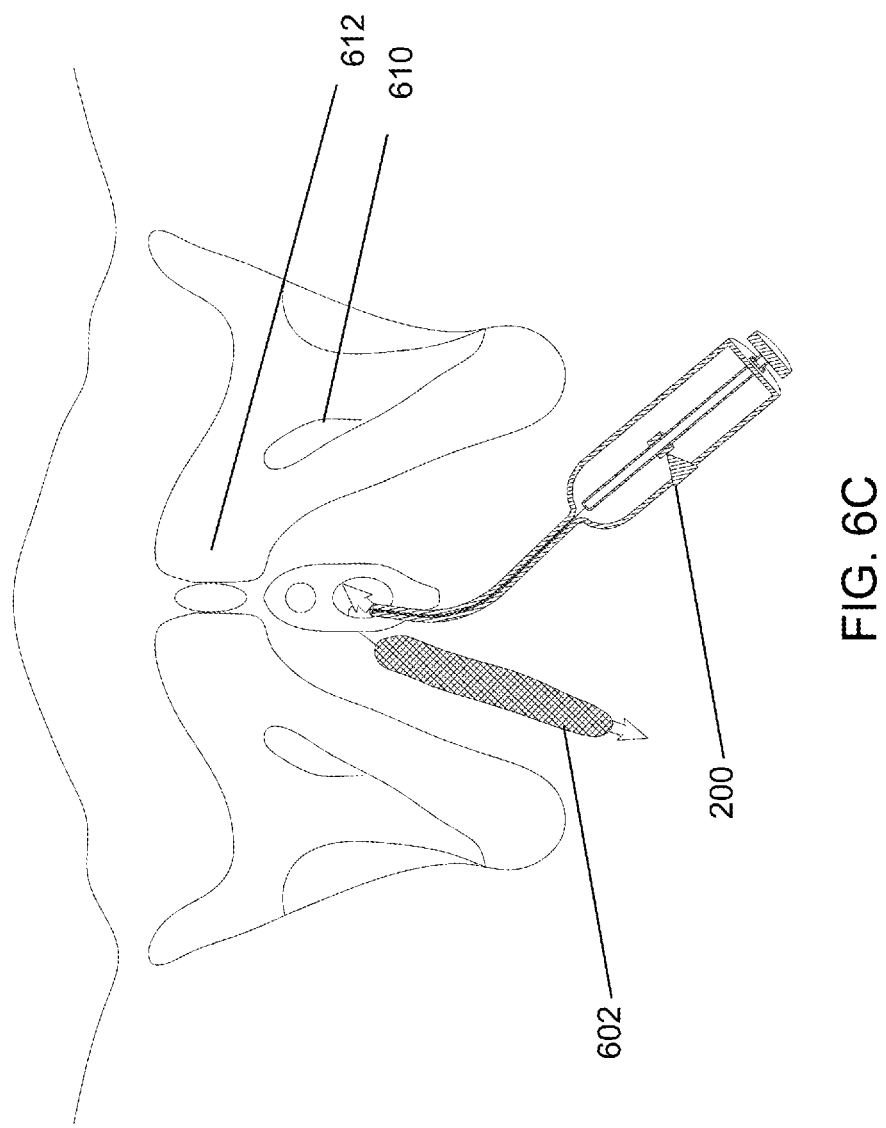
Figure 6D:
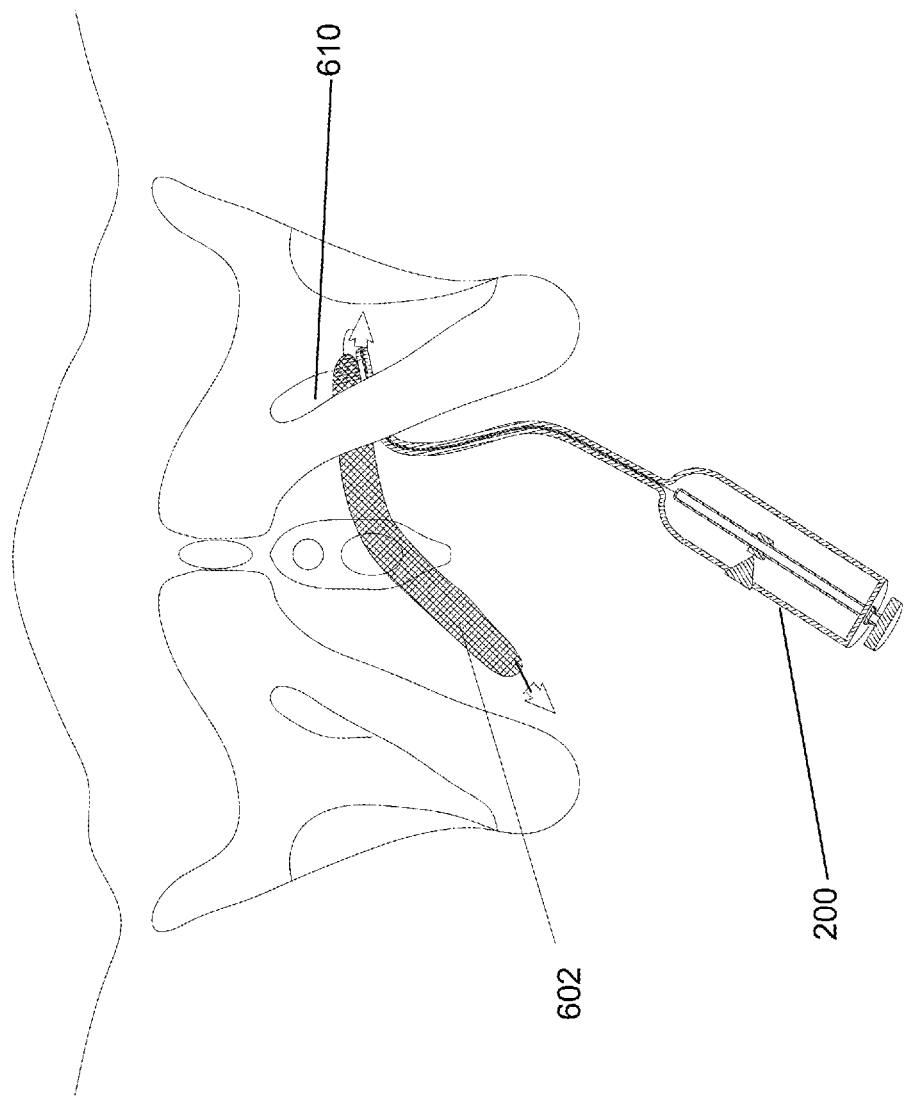
Figure 6E:
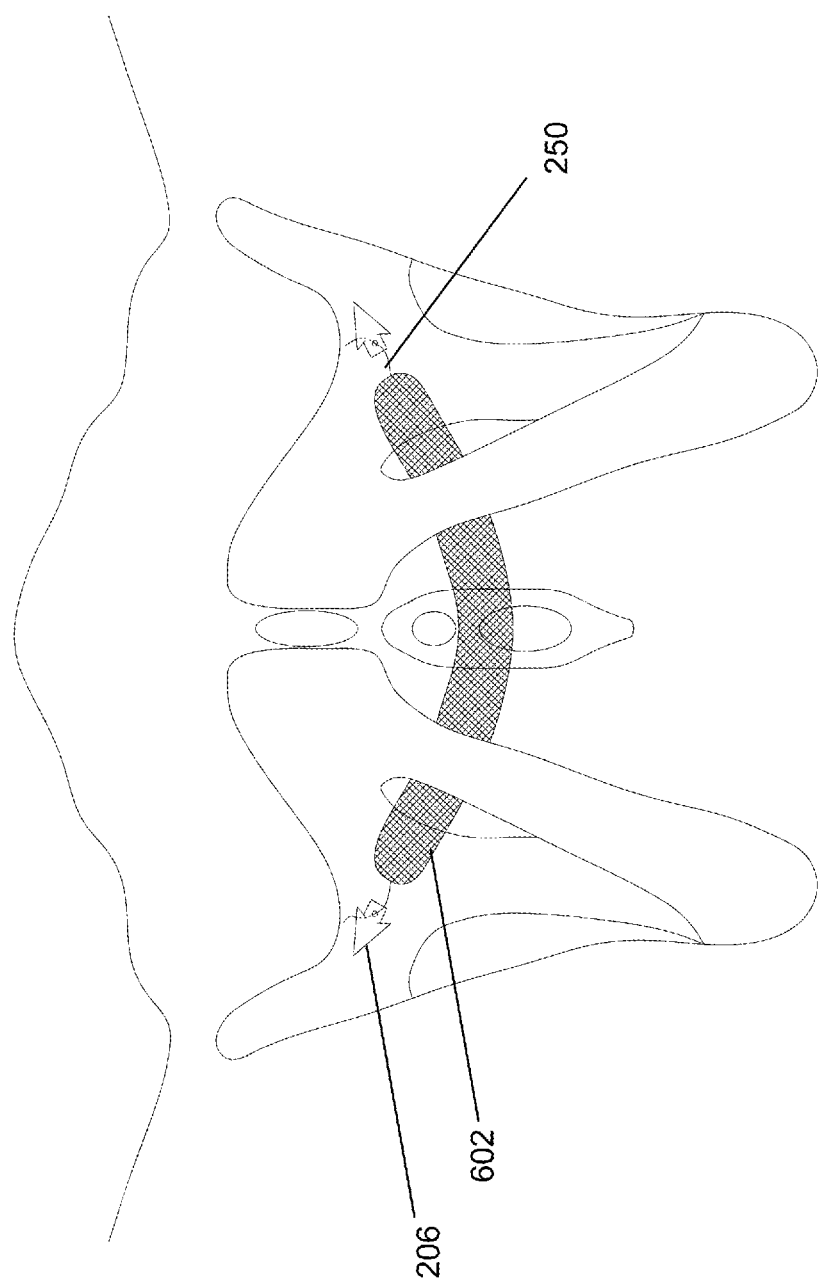

FIG. 6C illustrates delivery of the bodily implant 202 with the use of the medical assembly 200. In some embodiments, the bodily implant 202 is delivered inside the body and placed under the urethra 608 such that it supports the urethra 608. FIG. 6C shows a surgical stage when the bodily implant 202 is inside the body and not yet fixed to bodily tissues. After the bodily implant 202 is inserted and disposed inside the body, the carrier 206 is secured to the bodily tissue such as in or through the obturator muscles or membrane 610. The securing of the bodily implant 202 to the obturator muscles 610 (transburator approach) is illustrated in FIG. 6D. In certain other embodiments, the carrier 206 can be secured or fixed to other bodily tissues also such as close to a pubic bone 612 or sacrum of the patient. The first carrier and the second carrier are secured to bodily tissues. For example, the first carrier is secured to a first bodily tissue and the second carrier is secured to a second bodily tissue, and the implant 202 is placed at a desired position.

Figure 7:
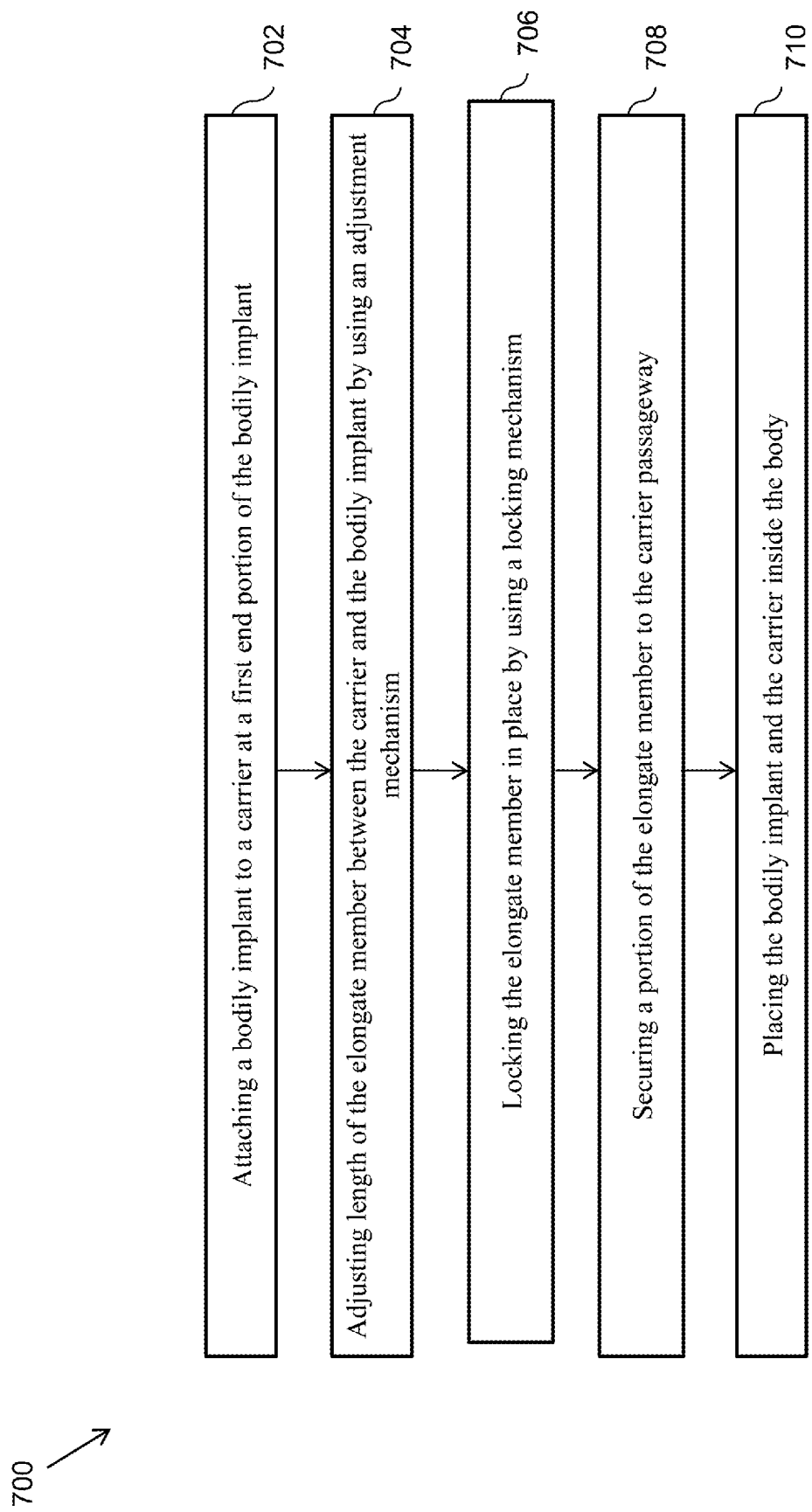
FIG. 7 illustrates a flowchart representing a method for delivery of a bodily implant in a patient's body, in accordance with an embodiment of the present invention.

FIG. 7 illustrates a flowchart representing a method 700 for delivery of the bodily implant 602 with the use of a medical assembly such as the medical assembly 200 in a patient's body, in accordance with an embodiment of the present invention.

Referring to FIG. 7, in conjunction with FIGS. 6A-6E, the method of delivery and placement of the bodily implant 202 with the use of a medical assembly 200 is described in accordance with an embodiment of the present invention. The medical assembly 200 is hereafter used to describe the method in an exemplary embodiment. However, it must be appreciated that other medical assemblies such as the medical assembly 100 or 500 may also be employed in a similar manner. The medical assembly 100, medical assembly 200, and the medical assembly 500 have already been described in conjunction with various figures above.

The method 700 includes attaching the bodily implant 602 to the carrier 206 at a first end portion of the bodily implant 602 at step 702. The carrier 206 is coupled to the insertion tool 204 such that the flexible elongate member 208 is configured to be disposed within the lumen 214 of the insertion tool 204 and extends through the passageway 240 formed within the carrier 206. The elongate member 208 is further coupled to the bodily implant 202, as shown. The insertion tool 204, carrier 206, elongate member 208, and the bodily implant 202 have been described in conjunction with FIG. 2.

The method 700 further includes adjusting length of the elongate member 208 between the carrier 206 and the bodily implant 602 at step 704 through the adjustment mechanism 224 internal to the insertion tool 204. The adjustment mechanism 224 has been described in conjunction with FIG. 2 while describing the medical assembly 200.

The length between the carrier 206 and the implant 602 can be adjusted by using the adjustment mechanism 224 that includes the knob 228 configured to be moved from a first position to a second position. The first and second positions can be rotatably obtained such as through a rotatable knob 228. In accordance with these embodiments, when the knob 228 is rotated between the first position and the second position, the elongate member 208 is forced to let or move inside or outside the lumen 214 of the insertion tool 204. The length of the elongate member 208 that moves into or out of the lumen 214 depends on the amount of rotation provided to the knob 228. Since, the elongate member 208 is coupled to the carrier 206 also, therefore, the elongate member 208 moves through the passageway 240 of the carrier 206 also when the knob 228 is rotated. The movement of the elongate member 208 through the carrier 206 will cause a change in the length of the elongate member 208 between the carrier 206 and the implant 202 since the elongate member 208 is further coupled to the implant 202 past the carrier 206. In some cases, the knob 228 can be rotated clockwise, for example, to decrease the length of the elongate member 208 between the carrier 206 and the implant 202. In other cases, the knob 228 can be rotated anti-clockwise to increase the length of the elongate member 208 between the carrier 206 and the implant 202. The clockwise and anti-clockwise rotation can be calibrated in an otherwise manner also such that rotation of the knob 228 in an anti-clockwise manner causes a decrease in length while the rotation in a clockwise manner causes an increase in the length.

In other embodiments, the first and second positions can be slidably obtained such as through a slidable knob similar to a push button. In accordance with these embodiments, the knob 228 can be slidably moved between the first and the second position by pushing or pulling it with respect to the handle 216. In accordance with these embodiments, when the knob 228 is slidably moved between the first position and the second position, the elongate member 208 is forced to let or move inside or outside the lumen 214 of the insertion tool 204. The length of the elongate member 208 that moves into or out of the lumen 214 depends on the amount of push or pull to cause sliding of the knob 228. Since, the elongate member 208 is coupled to the carrier 206 also, therefore, the elongate member 208 moves through the passageway 240 of the carrier 206 also when the knob 228 is pushed or pulled. The movement of the elongate member 208 through the carrier 206 will cause a change in the length of the elongate member 208 between the carrier 206 and the implant 202 since the elongate member 208 is further coupled to the implant 202 past the carrier 206. In some cases, the knob 228 can be pushed, for example, to decrease the length of the elongate member 208 between the carrier 206 and the implant 202. In other cases, the knob 228 can be pulled to increase the length of the elongate member 208 between the carrier 206 and the implant 202. The knob 228 can be calibrated in an otherwise manner also such that a push on the knob 228 causes a decrease in length while a pull on the knob 228 causes an increase in the length.

As described above, the movement of the knob 228 causes a change (either increase or decrease) in length of the elongate member 208 between the carrier 206 and the implant 602. The elongate member 208 can be locked at step 706 in place after adjustment by using the locking mechanism 226. The lock inside the locking mechanism 226 ensures that the second position of the knob 228 is restored unless there is a further adjustment in the length of the elongate member 208 through the adjustment mechanism 224. As described earlier, the locking mechanism 226 includes the gear 230, the push button 232, and the lock 234. In some embodiments, when the operator has adjusted the length of the elongate member 208 between the carrier 206 and the implant 202, the button is push from a location external to the lumen 214 of the insertion tool 204. This push causes an engagement of the button with the gear teeth such that the gear 230 gets engaged with the button. The lock 234 then causes the gear 230 engagement to be retained.

It must be appreciated the adjustment of the length of the elongate member 208 can be done directly from within the insertion tool 204. It must also be further appreciated that the adjustment of the length between the carrier 206 and the implant 202 is responsible for adjusting tension of the bodily implant 202. Therefore, it is understood that the implant tension adjustment can be done from within the insertion tool 204 of the medical assembly 200 without using any external device, system, element, or a procedural step.

The method further includes securing a portion of the elongate member 208 at step 708 such that one end of the secured portion is coupled to the carrier passageway 240 and the other end is coupled to the bodily implant 602. The secured portion defines the length of the elongate member 208 between the carrier 206 and the implant 602. The securing of the portion of the elongate member 208 can be done in various ways such as for example illustrated in FIGS. 3A-3C.

In an embodiment, the passageway 240 is defined in the form of the slot that has a substantially circular cross section at one end and a rectilinear cross section at the other end such that the rectilinear cross section is narrower than the circular cross section, as shown in FIG. 3A. The portion of the elongate member 208 is secured by first passing the elongate member 208 through the circular cross section 302 and then forced to pass through the narrower rectilinear cross section 304 where the elongate member 208 is choked and secured. In another embodiment, the passageway 240 is defined in the form of the slot and a teethed section having teeth configured to engage the elongate member 208 that passes through the slot and the teethed section, as shown in FIG. 3B. The portion of the elongate member 208 between the carrier 206 and the implant 202 is secured by passing the elongate member 208 through the circular cross section 306 and then through the teethed section 308 where the elongate member 208 is secured.

In another embodiment, the passageway 240 is defined in the form of the slot with a substantially circular cross section at one end and a rectilinear cross section at the other end such that the rectilinear cross section is narrower than the circular cross section. The elongate member 208 in this case is further configured to pass the slot and includes at least one knot 314 present at discrete locations on a portion of the elongate member 208 as shown. The portion of the elongate member 208 is secured by passing the elongate member 208 through the circular cross section 310 and then through the narrower rectilinear cross section 312 where the elongate member 208 is choked and secured because of the narrower cross section and the friction imposed by the knot 314 directly in contact with the slot. In accordance with this embodiment, the portion of the elongate member 208 between the carrier 206 and the implant 202 can be adjusted in discrete lengths of multiples of knot spacing (that is space between each knot). In some embodiments, the spacing between each knot can be same while in other embodiments, it can be different. In accordance with the use of this embodiment, a physician or an operator can easily know the amount of length that has been pulled through the passageway 240 and can therefore know the amount of tension applied to the bodily implant 602.

In accordance with at least some embodiments of the slot as described above, the securing of the elongate member 208 restricts movement of the elongate member 208 with respect to the carrier passageway 240 in a first direction and allows movement of the elongate member 208 with respect to the passageway 240 in a second direction. The first direction may be forward direction (pointing from the passageway 240 toward the implant 202) such that the portion of the elongate member 208 between the carrier 206 and the implant 202 can be pushed or moved away from the passageway 240 and toward the implant 202. The second direction may be backward direction (pointing from the passageway 240 toward the insertion tool 204) such that the portion of the elongate member 208 between the carrier 206 and the implant 202 can be pulled or moved toward the passageway 240 and toward the distal end of the insertion tool 204.

In an embodiment when the carrier 206 is a clamp similar to the clamps discussed above, the method of securing a portion of the elongate member may further include relocating the clamp over a portion of the elongate member for appropriate adjustments.

After the length of the elongate member 208 is adjusted, locked and secured to the passageway 240, the medical assembly 200 is inserted into the patient's body. The operator creates an incision in the patient's body for inserting the medical assembly 200 at step 706. The method of creating the incision and the location of the incision can vary based on the approach used. In one embodiment, the approach can be a retropubic approach. In another embodiment, the approach can be a transburator approach.

In some embodiments, the incision is made in an anterior vaginal wall and dissected bilaterally to an interior portion of an inferior pubic ramus. The medical operator grasps the handle 216 of the medical assembly 200 and inserts the needle 218 with the carrier 206 and implant 602 installed thereat, through the vaginal incision.

The insertion tool 204 can then be removed out of the body to leave the carrier 206 and the implant 202 inside the body. The method further includes placing the carrier 206 and the implant 602 within the patient's body at step 710.

After placement, the carrier 206 is anchored to the bodily tissues. In an embodiment, when the carrier 206 is the clamp, the carrier is clamped to the bodily tissue through the flaps by actuating the jaw with the use of the adjustment mechanism.

In various embodiments, the carrier is a first carrier that is attached to a first end portion of the bodily implant and fixed to a first bodily portion. The second end portion of the implant can include a second carrier that is placed at a second bodily portion inside the patient's body.

Once, the implant 202 is placed and the carriers 206 are anchored to the bodily portions, the elongate member 208 can finally be cut at some location between the insertion tool 204 and the carrier 206 thereby separating the insertion tool 204 from the implant and the carrier 206. The carrier 206 and the implant 202 are still coupled together via the elongate member 208. The insertion tool is removed from the patient's body such that the carrier or the carriers stays inside the body upon removal.

In some embodiments, a medical assembly configured to deliver and place a bodily implant inside a patient's body, the medical assembly includes an insertion tool configured to be inserted into a patient's body, the insertion tool having a proximal end portion and a distal end portion such that a portion between the distal end portion and the proximal end portion defines a lumen; a carrier configured to be coupled to the distal end portion of the insertion tool and configured to be disposed within a bodily tissue upon placement, wherein the carrier includes a passageway; and a flexible elongate member with a proximal end portion and a distal end portion, wherein the elongate member is configured to be disposed within the lumen of the insertion tool, the elongate member further configured to pass through the passageway of the carrier, and the elongate member configured to be coupled to the bodily implant such that a portion of the elongate member between the bodily implant and the carrier defines a length of the elongate member. The insertion tool includes an adjustment mechanism configured to adjust the length of the elongate member between the implant and the carrier and a locking mechanism configured to lock the elongate member within the insertion tool, and the length of the elongate member between the carrier and the bodily implant is configured to be fixed by securing the elongate member to the carrier passageway.

In some embodiments, the carrier is a dart having a tip portion configured to be fixed to the bodily tissue and configured to anchor the bodily implant with the bodily tissue upon placement.

In some embodiments, the carrier is a clamp configured to be coupled to the distal end portion of the insertion tool at its proximal end, the clamp further including a jaw having flaps configured to clamp the bodily tissue. In some embodiments, the clamp further includes a locking member configured to lock the flaps of the jaw into the bodily tissue.

In some embodiments, the insertion tool further includes a needle configured to be coupled to the carrier.

In some embodiments, the passageway of the carrier includes a slot with a substantially circular cross section at one end and a rectilinear cross section at the other end such that the rectilinear cross section is narrower than the circular cross section.

In some embodiments, the passageway of the carrier includes a slot, the carrier further including a teethed section having teeth configured to engage the elongate member that passes through the slot and the teethed section.

In some embodiments, the passageway of the carrier includes a slot with a substantially circular cross section at one end and a rectilinear cross section at the other end such that the rectilinear cross section is narrower than the circular cross section, the elongate member configured to pass the slot and includes a knot that is present at discrete locations on a portion of the elongate member.

In some embodiments, the bodily implant is a mesh based device configured to be coupled to the carrier and the insertion tool through the elongate member.

In some embodiments, the carrier is made of a material selected from the group consisting of polypropylene, plastic, bio absorbable, radiopaque, medical grade stainless steel, Acrylonitrile butadiene styrene and polycarbonate.

In some embodiments, the adjustment mechanism includes a knob configured to adjust the length of the elongate member by letting the elongate member in and out of the insertion tool, wherein the adjustment being possible from within the insertion tool.

In some embodiments, the locking mechanism includes a gear and a push button, wherein the push button is configured to engage gear teeth when pushed externally.

In some embodiments, the carrier is a first carrier configured to be attached to a first bodily tissue, the medical assembly further comprising a second carrier configured to be attached to a second bodily tissue.

In some embodiments, an insertion tool configured to deliver and place a bodily implant inside a patient's body, the insertion tool includes a handle and a needle extending from the handle, wherein a portion of the handle and the needle defines a lumen across their length, the lumen configured to receive a flexible elongate member, the elongate member configured to be coupled to the bodily implant; an adjustment mechanism having an adjustment knob provided on the handle that is configured to adjust length of the elongate member by letting a portion of the elongate member in or out of the lumen of the insertion tool; and a locking mechanism with a button, and a gear, the button configured to engage with the gear when pushed from a location external to the lumen.

In some embodiments, a method for placing a bodily implant in a patient's body, the method includes (1) adjusting length of an elongate member between a carrier and the implant by operating a knob provided on an insertion tool such that operating the knob changes the length of the elongate member between the carrier and the implant by letting a portion of the elongate member in or out of the insertion tool, wherein the carrier is configured to be disposed within a bodily tissue upon placement inside the body; (2) locking the elongate member within the insertion tool, after the length between the carrier and the implant is adjusted, by pressing a button provided on the insertion tool; (3) securing the length of the elongate member between the carrier and the implant to a carrier passageway provided in the carrier such that one end of the secured length is coupled to the carrier passageway and the other end is coupled to the bodily implant; and (4) placing the bodily implant and the carrier inside the body.

In some embodiments, the locking mechanism includes a gear, the method further comprising engaging the gear with the button after the button is pressed.

In some embodiments, the carrier is a clamp, the clamp further including a jaw having flaps configured to come in contact with one another, the method further comprising clamping a bodily tissue within the flaps by actuating the jaw with the use of the knob.

In some embodiments, the securing of the portion of the elongate member further comprises relocating the clamp along a length of the elongate member.

In some embodiments, the method includes placing the carrier into the obturator internus muscle through a single midline incision in a vaginal wall.

In some embodiments, the carrier is a first carrier attached to a first end portion of the bodily implant and configured to be placed at a first bodily portion, the method further comprising placing the second carrier at a second bodily portion inside the patient's body, the second carrier attached to a second end portion of the bodily implant.

In some embodiments, the method includes removing the insertion tool from the patient's body such that the carrier stays inside the body upon removal.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. A medical assembly configured to deliver and place a bodily implant inside a patient's body, the medical assembly comprising:
   an insertion tool configured to be inserted into a patient's body, the insertion tool including a handle and a needle coupled to a distal end portion of the handle, the insertion tool including a shaft at least partially disposed within a lumen of the handle, the shaft having a distal end portion and a proximal end portion;
   a carrier configured to be coupled to a distal end portion of the needle, the carrier configured to be disposed within a bodily tissue upon placement, the carrier defining a passageway; and
   an elongate member having a proximal end portion and a distal end portion, the proximal end portion of the elongate member being coupled to the distal end portion of the shaft at a location inside the lumen of the handle, the elongate member extending through a lumen of the needle and the passageway of the carrier, the distal end portion of the elongate member configured to be coupled to a bodily implant, the insertion tool including an adjustment mechanism coupled to the proximal end portion of the shaft, the adjustment mechanism being disposed outside the lumen of the handle, the adjustment mechanism including a rotation member configured to rotate, wherein rotation of the rotation member is configured to move the shaft with respect to the handle and move the elongate member in and out of the insertion tool such that a length of the elongate member between the bodily implant and the carrier is adjusted, the insertion tool further including a locking mechanism configured to lock the elongate member within the insertion tool.

2. The medical assembly of claim 1, wherein the carrier includes a dart having a tip portion configured to be attached to the bodily tissue and configured to anchor the bodily implant within the bodily tissue upon placement.

3. The medical assembly of claim 1, wherein the carrier includes a clamp, the clamp having a jaw having flaps configured to clamp the bodily tissue.

4. The medical assembly of claim 3, wherein the clamp further includes a locking member configured to lock the flaps of the jaw into the bodily tissue.

5. The medical assembly of claim 1, wherein the passageway of the carrier includes a slot with a substantially circular cross section at one end and a rectilinear cross section at the other end such that the rectilinear cross section is narrower than the circular cross section.

6. The medical assembly of claim 1, wherein the passageway of the carrier includes a slot, the carrier further including a teethed section having teeth configured to engage the elongate member that passes through the slot and the teethed section.

7. The medical assembly of claim 1, wherein the passageway of the carrier includes a slot with a substantially circular cross section at one end and a rectilinear cross section at the other end such that the rectilinear cross section is narrower than the circular cross section, the elongate member configured to pass through the slot and includes a knot that is disposed at a discrete location on a portion of the elongate member.

8. The medical assembly of claim 1, wherein the bodily implant is a mesh based device configured to be coupled to the carrier and the insertion tool through the elongate member.

9. The medical assembly of claim 1, wherein the carrier is made of a material selected from the group consisting of polypropylene, plastic, bio absorbable, radiopaque, medical grade stainless steel, Acrylonitrile butadiene styrene and polycarbonate.

10. The medical assembly of claim 1, wherein the rotation member includes a knob.

11. The medical assembly of claim 1, wherein the locking mechanism includes a gear and a push button, the push button extending from an outer surface of the handle, wherein the push button is configured to engage gear teeth of the gear when the push button is activated.

12. The medical assembly of claim 1, wherein the carrier is a first carrier configured to be attached to a first bodily tissue, the medical assembly further comprising a second carrier configured to be attached to a second bodily tissue.

13. An insertion tool configured to deliver and place a bodily implant inside a patient's body, the insertion tool comprising:

a handle defining a first lumen;

a needle extending from a distal end portion of the handle, the needle configured to be coupled to a carrier, the needle defining a second lumen, the second lumen extending from the first lumen of the handle, the first lumen having a diameter larger than a diameter of the second lumen, the first lumen and the second lumen configured to receive an elongate member coupled to an implant;

a shaft at least partially disposed within the first lumen of the handle, the shaft having a proximal end portion and a distal end portion, the distal end portion of the shaft being coupled to a proximal end portion of the elongate member at a location inside the first lumen of the handle;

an adjustment mechanism having a rotating member coupled to the proximal end portion of the shaft, the rotating member being disposed outside the first lumen of the handle, the rotating member extending from a proximal end portion of the handle, the rotating member configured to rotate, wherein rotation of the rotating member is configured to move the shaft with respect to the handle and move the elongate member in and out of the insertion tool such that a length of the elongate member between the implant and the carrier is adjusted; and a locking mechanism having a button and a gear, the button configured to extend from a surface of the handle, the button configured to engage with the gear to lock the elongate member when the button is activated.

14. A method for placing a bodily implant in a patient's body, the method comprising:

adjusting a length of an elongate member between a carrier and the implant by operating a knob provided on an insertion tool such that operating the knob changes the length of the elongate member between the carrier and the implant by letting a portion of the elongate member in or out of the insertion tool, wherein the carrier is configured to be disposed within a bodily tissue upon placement inside the body;

locking the elongate member within the insertion tool, after the length between the carrier and the implant is adjusted, by pressing a button provided on the insertion tool;

securing the length of the elongate member between the carrier and the implant to a carrier passageway provided in the carrier such that one end of the secured length is coupled to the carrier passageway and the other end is coupled to the bodily implant; and placing the bodily implant and the carrier inside the body including placing the carrier into an obturator internus muscle.

15. The method of claim 14, wherein the locking the elongate member within the insertion tool includes engaging a gear with the button after the button is pressed.

16. The method of treatment of claim 14, wherein the carrier is a clamp, the clamp further including a jaw having flaps configured to come in contact with one another, the method further comprising clamping a bodily tissue within the flaps by actuating the jaw with the use of the knob.

17. The method of claim 16, wherein the securing the elongate member further comprises relocating the clamp along the length of the elongate member.

18. The method of claim 14, wherein the carrier is placed into the obturator internus muscle through a single midline incision in a vaginal wall.

19. The method of claim 14, wherein the carrier is a first carrier attached to a first end portion of the bodily implant and configured to be placed at a first bodily portion, the method further comprising placing a second carrier at a second bodily portion inside the patient's body, the second carrier attached to a second end portion of the bodily implant.

* * * * *